United States Patent
Malo

(10) Patent No.: US 6,566,067 B2
(45) Date of Patent: May 20, 2003

(54) HIGH FIDELITY PCR CLONING

(75) Inventor: Madhu Sudan Malo, Watertown, MA (US)

(73) Assignee: SyntheGen Systems, Inc., Medford, MA (US)

( * ) Notice: Subject to any disclaimer, the term of this patent is extended or adjusted under 35 U.S.C. 154(b) by 0 days.

(21) Appl. No.: 09/783,106

(22) Filed: Feb. 14, 2001

(65) Prior Publication Data

US 2002/0160462 A1 Oct. 31, 2002

(51) Int. Cl.$^7$ .......................... C12Q 1/68; C12P 19/34; C07H 21/04
(52) U.S. Cl. ................. 435/6; 435/91.2; 435/91.21; 536/24.33
(58) Field of Search .................. 435/6, 91.2, 91.21; 536/24.33

(56) References Cited

U.S. PATENT DOCUMENTS

| | | | | |
|---|---|---|---|---|
| 4,683,195 A | * | 7/1987 | Mullis et al. | 435/6 |
| 4,683,202 A | * | 7/1987 | Mullis | 435/91 |
| 4,965,188 A | * | 10/1990 | Mullis et al. | 435/6 |
| 5,487,993 A | * | 1/1996 | Herrnstadt et al. | 435/172 |
| 5,856,144 A | * | 1/1999 | Mierendorf et al. | 435/91 |
| 5,891,687 A | * | 4/1999 | Schlieper et al. | 935/172 |

OTHER PUBLICATIONS

Cline J et al. PCR fidelity of pfu DNA polymerase and other thermostable DNA polymerases. Nucleic Acids Res., vol. 24 (18), pp. 3546–3551, 1996.*
Eckert et al. DNA polymerase fidelity and the polymerase chain reaction. PCR Methods and Applications, vol. 1(1), pp. 17–24, 1991.*
Spitzweg c et al. Analysis of human sodium iodide symporter gene expression in extrathyroidal tissues and cloning of its cDNAs from salivary gland, mammary gland and gastric mucosa. J Clin Endocrinol Metab., vol. 83(5):1746–1751, 1998.*
Clontech Catalog. Cloning kits and cDNA. Clontech Catalog. pp. 54–55, 2000.*
Andre et al. Fidelity and mutational spectrum of Pfu DNA polymerase on a human mitochondrial DNA sequence. Genome Res. 7, 843–852, 1997.*
Cariello et al. Fidelity of Thermococcus litoralis DNA polymerase (Vent TM) in PCR determined by denaturing gradient gel electrophoresis. Nucl. Acids Res., 19, 4193–4198, 1991.*
Cline et al. PCR fidelity of Pfu DNA polymerase and other thermostable DNA polymerases. Nucl. Acids Res., 24, 3546–3551, 1996.*
Keohavong et al. DNA amplification in vitro using T4 DNA polymerase, 7, 63–70, 1988.*
Keohavong P. and Thilly W.G. Fidelity of DNA polymerases in DNA amplification. Proc.NAtl.Acad.Sci.USA, 86, 9253–9257, 1996.*
Kong et al. Characterization of DNA polymerases from the hyperthermophile arches theromcoccus litoralis. Vent DNA polymerase, steady state kinetics, thermal stability, processivity, strand displacement, and exonuclease activities, J. Biol. chem, 268, 1965–75, 1993.*
Kunkel T.A. and Bebenek K. DNA replication fidelity. Annu.Rev.Biochem., 69, 497–529, 2000.*
Kunkel et al. On the fidelity of DNA replication. The accuracy of T4 DNA polymerases in copying phi X 174 DNA in vitro. J. Biol. Chem., 259, pp. 1539–1545, 1984.*
Leob L.A. and Kunkel T.A. Fidelity of DNA syntheisis. Annu. Rev. Biochem. 52, 429–457, 1982.*
Lundberg et al. High–fidelity amplification using a thermostable DNA polymerase isolated from the pyroccocus furiosus. Gene 180, 1–6, 1991.*
Malo M.S. and Hussain Z. pRGR: a positive selection vector system for direct cloning of PCR amplified DNA fragments. USPTO application no. 09/722219, 2000.*
Mullis K.B. and Faloona FA. Specific synthesis of DNA invitro via polymerase–catalyzed chain reaction. Methods Enzymol, 55, pp. 335–350, 1987.*
Reiss et al. The effect of replication errors on the mismatch analysis of PCR–amplified DNA. Nucl. Acids Res. 18, 973–978, 1990.*
Sambrook et al. Molecular Cloning: A Laboratory Mannual, Cold Spring Harbor Laboratory, Cold Spring Harbor, New York, 1989.*
Saiki et al. Enzymatic amplification of beta–globin genomic sequences and restriction site analysis for diagnosis of sickle cell anemia. Science, 230, 1350–1354, 1985.*

* cited by examiner

Primary Examiner—Jeffrey Fredman
Assistant Examiner—Suryaprabha Chunduru
(74) Attorney, Agent, or Firm—Ropes & Gray

(57) ABSTRACT

The present invention describes a methodology for generating high fidelity PCR products, and also cloning of such high fidelity PCR products in a suitable vector. Generation of polymerase-induced mutant fraction of target sequences during PCR amplification is linearly proportional to the number of doublings of the target sequences. Thus the high fidelity PCR products are generated by minimizing the number of doublings of the target nucleic acid sequences during PCR amplification. Minimization of number of doublings of the target sequences is achieved by reducing the number of cycles of PCR amplification of the target sequences. The high fidelity PCR products thus obtained are then cloned into a suitable vector. As an example, a 960 bp target sequence from *E. coli* DNA was PCR-amplified only for 3 cycles, and it was then directly cloned into a positive selection cloning vector pRGR2Ap. The functional analysis of the inserts in all clones showed that the clones carried functionally wild-type DNA fragments, and hence the inserts most probably carry no mutation. Cloning of PCR products obtained from 3 cycles of amplification, instead of 30 cycles of amplification, theoretically achieves 10-fold reduction of mutations in the cloned fragments. The invention also contemplates cloning of a target cDNA obtained by primer extension.

19 Claims, No Drawings

SEQUENCE LISTING

```
<160> NUMBER OF SEQ ID NOS: 2

<210> SEQ ID NO 1
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Forward primer LC1261RGRF

<400> SEQUENCE: 1
```

-continued

```
tggtaagctt gcggccgcaa aggccacaat ttcacacagg aaacagctat g         51
```

<210> SEQ ID NO 2
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Reverse primer LC2220R

<400> SEQUENCE: 2

```
ccgcacgata gagattcggg atttcggcgc                                 30
```

HIGH FIDELITY PCR CLONING

STATEMENT REGARDING FEDERALLY SPONSORED RESEARCH OR DEVELOPMENT

Not Applicable

REFERENCE TO A MICROFICHE APPENDIX

Not Applicable

REFERENCE TO SEQUENCE LISTING

Not Applicable

FIELD OF THE INVENTION

The present invention relates to a methodology for high fidelity cloning of target nucleic acids. The invention involves application of polymerase chain reaction (PCR) for a few cycles, which minimizes number of doublings of target sequences, and hence greatly reduces generation of polymerase-induced mutant fraction in PCR products. The invention also describes cloning of such high fidelity PCR products in a positive selection vector.

BACKGROUND OF THE INVENTION

Polymerase chain reaction or PCR (Saiki et al., 1985, Science 230, 1350–1354; Mullis and Faloona, 1987, Method Enzymol. 155, 335–350; U.S. Pat. Nos. 4,683,195; 4,683,202 and 4,965,188) has revolutionized amplification of target nucleic acids. The technique involves repeated cycles of denaturation of template nucleic acid molecules, sequence-specific primer annealing and primer extension using DNA polymerase thus resulting in an exponential amplification of the target nucleic acids. Usually, 30 cycles of PCR result in one million-fold amplification of target sequences from 20 doublings.

The PCR product itself could be used for diagnosis, quantitation of the template, direct sequencing and some other applications (U.S. Pat. Nos. 5,856,144; 5,487,993 and 5,891,687). However, for applications such as mutation analysis, identification of polymorphic transcripts, making RNA probes, sequencing, gene expression etc., usually a large quantity of DNA is needed. Thus it is necessary to isolate a bacterial clone carrying the PCR generated target DNA fragment in a cloning vector.

For correct structural and functional analyses it is fundamentally important to clone wild-type nucleic acids. Cloning of wild-type nucleic acids is critical for mutation analysis, identification of polymorphic transcripts and sequencing. It is also of paramount importance that for accurate functional analysis a true copy of the desired gene should be cloned in a suitable expression vector. However, an inherent disadvantage of DNA amplification using PCR is the introduction of mutations by the polymerases during synthesis of new DNA (Kunkel and Bebenek, 2000, Annu. Rev. Biochem. 69, 497–529; Andre et al., 1997, Genome Res. 7, 843–852; Cline et al., 1996, Nucl. Acids Res. 24, 3546–3551; Kong et al., 1993, J. Biol. Chem. 268, 1965–1975; Cariello et al., 1991, Nucl. Acids Res. 19, 4193–4198; Lundberg et al., 1991, Gene 180, 1–6; Reiss et al., 1990, Nucl. Acids Res. 18, 973–978; Keohavong and Thilly, 1989, Proc. Natl. Acad. Sci. USA 86, 9253–9257; Keohavong et al., 1988, DNA 7, 63–70; Kunkel et al., 1984, J. Bio. Chem. 259, 1539–1545; Loeb and Kunkel, 1982, Annu. Rev. Biochem. 52, 429–457). The total mutant fraction in a newly synthesized PCR-amplified DNA pool depends on the length of target sequence, error rate of a DNA polymerase, and number of doublings of the target sequence (Kunkel and Bebenek, 2000, Annu. Rev. Biochem. 69, 497–529; Andre et al., 1997, Genome Res. 7, 843–852; Cariello et al., 1991, Nucl. Acids Res. 19, 4193–4198; Reiss et al., 1990, Nucl. Acids Res. 18, 973–978). The error rates of different DNA polymerases vary from $1.3 \times 10^{-4}$ to $6.5 \times 10^{-7}$ mutant per basepair per doubling (Andre et al., 1997, Genome Res. 7, 843–852; Cline et al., 1996, Nucl. Acids Res. 24, 3546–3551; Cariello et al., 1991, Nucl. Acids Res. 19, 4193–4198; Keohavong and Thilly, 1989, Proc. Natl. Acad. Sci. USA 86, 9253–9257). For a million-fold amplification of target sequences 20 doublings are required, which are usually achieved by 30 cycles of PCR amplification. For a specific target sequence the increase of mutation fraction in the PCR-amplified DNA pool is a linear function of the number of doublings of the target sequence provided that the error rate of DNA polymerase remains constant under the specific PCR conditions (Kunkel and Bebenek, 2000, Annu. Rev. Biochem. 69,497–529; Andre et al., 1997, Genome Res. 7, 843–852; Cariello et al., 1991, Nucl. Acids Res. 19, 4193–4198; Reiss et al., 1990, Nucl. Acids Res. 18, 973–978).

The present methods of PCR cloning involve usually cloning of PCR products obtained after 20 doublings of target sequences thus resulting in generation of significant number of mutant clones, especially in case of cloning large target DNA fragments. Consequently, sometime rigorous sequencing of many clones is required to isolate a correct clone, and very often site-directed mutagenesis is necessary to correct a mutant clone. Furthermore, failure of PCR cloning of a correct sequence necessitates laborious screening of genomic or cDNA libraries, which usually represent correct sequences.

OBJECTS OF THE INVENTION

The primary object of this invention is to develop a methodology for cloning of high fidelity PCR products that contain no or minimum mutations. The invention aims to generate high fidelity PCR products by amplifying target sequences only for a few cycles, which minimizes number of doublings of target sequences, and hence greatly reduces polymerase-induced mutant fraction in PCR products. The invention further aims to clone high fidelity PCR products in a suitable vector.

Elimination of disadvantages associated with present protocols of PCR cloning and library screening is greatly desirable. The present invention aims to achieve a milestone advancement in cloning of a target sequence with no mutation.

SUMMARY OF THE INVENTION

The present invention describes a methodology of high fidelity PCR cloning of target nucleic acids. During PCR amplification of target nucleic acid sequences the polymerase-induced mutation fraction is linearly proportional to the number of doublings of the target sequences. The invention uses PCR on target nucleic acid sequences only for a few cycles, which minimizes number of doublings of target sequences, and hence greatly reduces polymerase-induced mutant fraction in PCR products. The high fidelity PCR products thus obtained are then cloned into a suitable vector. As an example, a 960 bp target sequence from E. coli DNA was amplified using PCR only for 3 cycles, and it was then directly cloned into a positive selection cloning vector pRGR2Ap. All insert-carrying clones showed cloning of functionally wild-type target DNA sequences, which indicated that the cloned target sequences most probably contained no mutation. Cloning of PCR products obtained from 3 cycles of amplification, instead of 30 cycles of amplification, theoretically achieves 10-fold reduction of mutations in the cloned fragments. The invention also envisions cloning of high fidelity products of primer extension.

BRIEF DESCRIPTION OF FIGURES

Not Applicable

DETAILED DESCRIPTION OF THE INVENTION

The present invention is directed to develop a PCR cloning method that will greatly reduce, if not eliminate, the number of mutant clones that are observed with present PCR cloning experiments. Presently, in a typical PCR cloning experiment PCR products obtained usually from 30 cycles of PCR amplification are used in cloning. PCR amplification of target sequences for 30 cycles usually result in one million-fold amplification of target sequences, which is equivalent to 20 doublings of target sequences. The increase in total mutant fraction in PCR products pool is a linear function of the number of doublings of target sequences (Kunkel and Bebenek, 2000, Annu. Rev. Biochem. 69, 497–529; Andre et al., 1997, Genome Res. 7, 843–852; Cariello et al., 1991, Nucl. Acids Res. 19, 4193–4198; Reiss et al., 1990, Nucl. Acids Res. 18, 973–978). The invention describes generation of high fidelity PCR products by amplifying the target sequences only for a few cycles, which minimizes number of doublings of target sequences, and hence greatly reduces polymerase-induced mutant fraction in PCR products. The invention further describes cloning of such high fidelity PCR products in a suitable vector.

The amount of DNA obtained after a few cycles of PCR amplification is very small, and hence cloning of such small amount of DNA should give only a few colonies even at the most efficient conditions of ligation and transformation. Thus it was decided to clone such high fidelity PCR products into a positive selection cloning vector pRGR2Ap, which gives a very few false positive background colonies (Malo and Husain, 2000, USPTO application #09/722219). The positive selection vector pRGR2Ap has been developed based on reconstruction of the ampicillin resistance reporter gene. When the last (position 286) amino acid tryptophan (encoded by 5'-TGG-3') of ampicillin resistance gene product β-lactamase is replaced by valine (encoded by 5'-GTG-3') β-lactamase becomes functionally inactive. The sequence 5'-GTG-3' is a part of the Pml I restriction endonuclease cleavage site 5'-CACGTG-3', which is a unique cloning site in this vector. Thus upon Pml I restriction endonuclease cleavage 5'-CAC-3' and 5'-GTG-3' are created at the 3' and 5' ends respectively of the linearized blunt-ended vector. A PCR primer carrying the nucleotides 5'-TGGTAA-3' at its 5' end is used in PCR. When the resulting blunt-ended PCR products are ligated to the vector the reporter ampicillin resistance gene is reconstructed correcting the mutation. The nucleotides 5'-TAA-3' constitute the stop codon for the ampicillin resistance gene. Subsequent transformation of a host cell with the recombinant vector (carrying an insert DNA) produces functionally active β-lactamase, which confers resistance to ampicillin. Hence only the recombinant clones grow in an ampicillin-containing medium, and cloning in pRGR2Ap is unidirectional. Insertional reconstruction of the ampicillin resistance reporter gene in pRGR2Ap also minimizes generation of false positive clones arising from recircularization of linearized vectors digested by contaminating exonucleases present in restriction endonucleases, ligases, DNA polymerases and other reagents. In case of other available toxin-based positive selection vectors or lacZ-based chromogenic vectors, false positive clones arise from recircularization of linearized exonuclease-digested vectors, which could have lost some bases from their ends due to exonuclease digestion. Recircularized exonuclease-digested pRGR2Ap should not produce functionally active β-lactamase, and hence should not grow in a medium containing ampicillin thus greatly reducing exonuclease-induced false positive clones. The vector pRGR2Ap carries the tetracycline resistance gene as the selectable marker gene.

EXAMPLE 1

General Techniques of Molecular Biology

Unless otherwise indicated, the molecular biology techniques related to this invention are described in Sambrook et al., Molecular Cloning: A Laboratory Manual, Cold Spring Harbor Laboratory, Cold Spring Harbor, N.Y., 1989.

For enzymatic amplification of a target DNA fragment PCR was performed (Saiki et al., 1985, Science 230, 1350–1354; Mullis and Faloona, 1987, Method Enzymol. 155, 335–350) using a thermal cycler (Perkin Elmer Cetus, Foster City, Calif., USA) according to the manufacturer's instructions.

The thermostable Pfu DNA polymerase (Stratagene, La Jolla, Calif., USA) was used according to the recommendations of the supplier, and DNA restriction digestion was performed according o the specifications of the manufacturer (New England Biolabs, Beverly, Mass., USA). T4 DNA ligase was obtained from Life Technologies/GIBCO-BRL (Rockville, Md., USA), and used according to the instructions of the manufacturer. E. coli DNA was obtained from Sigma (St. Louis, Mo., USA). Oligonucleotides were synthesized by Biosource International (Camarillo, Calif., USA). Transformation of the commercially available competent host cells was carried out as per the instructions of the supplier (Life Technologies/GIBCO-BRL, Rockville, Md., USA). The transformants were plated onto LB agar medium (Life Technologies/GIBCO-BRL, Rockville, Md., USA) containing ampicillin (100 µg/ml; Sigma, St. Louis, Mo., USA) and/or tetracycline (12.5 µg/ml; Sigma, St. Louis, Mo., USA). For small scale preparation of plasmid DNA, host cells were grown on LB broth (Life Technologies/GIBCO-BRL, Rockville, Md., USA) containing ampicillin (100 µg/ml) and/or tetracycline (12.5 µg/ml), and DNA was prepared using alkaline lysis method.

High Fidelity PCR

It was decided to clone high fidelity PCR products of the 5' end of E. coli lacZ gene that produces the α peptide of β-galactosidase, the product of lacZ. The lac⁻ E. coli host cell DH5 α produces nonfunctional β-galactosidase, which, when complemented with the α peptide, becomes functional. The amount of α peptide produced even from basal level expression of lacZ complements the nonfunctional β-galactosidase in DH5α, and thus the transformant colonies harboring recombinant vectors turn blue in presence of X-gal, the substrate for β-galactosidase. Hence cloning of the 5' end of the lacZ gene would allow functional analysis of the cloned sequences thus indicating the extent of mutations in different clones. The following primers were used in PCR amplification of the above mentioned DNA fragment:

Forward Primer LC1261RGRF: (SEQ ID NO:1)
5'-TGG TAA GCT TGC GGC CGC AAA GGC CAC AAT TTC ACA CAG GAA ACA GCT ATG-3' (51 bases)
Reverse Primer LC2220R: (SEQ ID NO:2)
5'-CCG CAC GAT AGA GAT TCG GGA TTT CGG CGC-3' (30 bases)

Primers LC1261RGRF (SEQ ID NO:1) and LC2220R (SEQ ID NO:2) would PCR-amplify a 960 bp fragment from *E. coli* DNA. The forward primer LC1261RGRF (SEQ ID NO:1) carries 5'-TGGTAA-3' sequence at the 5' end, and hence the PCR product obtained using primers LC1261RGRF (SEQ ID NO:1) and LC2220R (SEQ ID NO:2) could be unidirectionally cloned into pRGR2Ap digested by Pml I thus reconstructing the ampicillin resistance gene in the recombinant clones. The vector pRGR2Ap carries Not I and Sfi I sites upstream of the cloning site Pml I, and the forward primer LC1261RGRF (SEQ ID NO:1) also carries Not I and Sfi I restriction sites. Thus the insert in a recombinant clone could be released by Not I or Sfi I restriction digestion.

The PCR conditions are given below:

1.0 μg *E. coli* DNA
0.01 μM forward primer LC1261RGRF (SEQ ID NO:1)
0.01 μM reverse primer LC2220R (SEQ ID NO:2)
0.2 mM dNTPs (equimolar mixture of dATP, dGTP, dCTP and dTTP)
1.0 μl of 10×low salt buffer for Pfu DNA polymerase
2.5 U Pfu DNA polymerase
Distilled water making total volume up to 10 μl To prevent evaporation during PCR cycling one drop of mineral oil was added overlaying the PCR mixture.

The PCR cycling conditions are given below:

2 min at 94° C., then 3 cycles of 1 min at 94° C., 5 min at 55° C., 3 min at 72° C., and then followed by a final extension step of 5 min at 72° C.

Ligation of the High Fidelity PCR Products 10.0 μl of high fidelity PCR products
3.0 μl of 5× ligation buffer
1.0 μl (1 ng) of Pml I digested pRGR2Ap
1.0 μl (5 U) of T4 DNA ligase Ligation was performed for overnight at 16° C.

Transformation of UltraMaxefficiency DH5α *E. coli* Host Cells

An aliquot of 3 μl ligation mix was used to transform 100 μl UltraMaxefficiency DH5α (Life Technologies/GIBCO-BRL, Rockville, Md., USA) *E. coli* host cells according to the recommended protocols. The transformation mix was incubated for 30 min on ice, followed by heat shock at 42° C. for 50 sec, 2 min on ice, addition of 1.0 ml of SOC medium (Life Technologies/GIBCO-BRL, Rockville, Md., USA), and incubation at 37° C. for 1 hr. The transformant cells were harvested by brief centrifugation, and were then resuspended in 100 μl of SOC medium. The resuspended cells were plated onto LB agar plates containing 100 μg/ml ampicillin, 12.5 μg/ml tetracycline and 40 μg/ml X-gal, and incubated overnight at 37° C. As expected, small number of transformant colonies grew, most of which were blue. The result of the experiment is shown in Table 1. All transformant clones were individually cultured in 5 ml LB broth containing 100 μg/ml ampicillin and 12.5 μg/ml tetracycline for overnight at 37° C. Small scale plasmid DNA was isolated using standard alkaline lysis method (Sambrook et al., Molecular Cloning: A Laboratory Manual, Cold Spring Harbor Laboratory, Cold Spring Harbor, N.Y., 1989). The isolated plasmid DNA was characterized by Not I or Sfi I restriction endonuclease digestion, which should release the insert fragment.

TABLE 1

| Total number of colonies | Number of blue colonies | White colonies carrying insert[a] | Blue colonies releasing insert[b] |
|---|---|---|---|
| 17 | 14 | 0 | 14 |

[a]The plasmids were digested with either Not I or Sfi I, and none of the restriction enzymes either released the insert or showed increased size of the plasmid compared to the size of the cloning vector pRGR2Ap.
[b]The plasmids were digested with either Not I or Sfi I, and each restriction enzyme released the insert.

Table 1 shows that the high fidelity PCR products were successfully cloned, and pRGR2Ap was a very useful vector for such cloning. Each of the blue clones released the insert, whereas, none of the background white clones carried any insert. Turning of the insert-carrying clones blue shows that the inserts were functionally wild-type, and hence the inserts most probably carry no mutation.

In conclusion, a methodology has been established for cloning a target nucleic acid sequence with no or minimum mutations, wherein such high fidelity cloning is achieved by cloning of PCR products generated from minimum number of doublings of the target sequence due to a fewer cycles of PCR amplification. In theory, cloning of PCR products obtained from 3 cycles of amplification, instead of 30 cycles of amplification, achieves 10-fold reduction of mutations in the cloned fragments. The invention also contemplates cloning of a target cDNA obtained by primer extension.

I claim:

1. A method of cloning a high fidelity polymerase chain reaction (PCR) product comprising:
providing a target nucleic acid as a template for PCR amplification;
generating high fidelity PCR product from 1–10 doublings of the target nucleic acid by performing 1–10 cycles of PCR; and
cloning a high fidelity PCR product into a vector;
wherein the target nucleic acid is provided in an amount no greater than about 0.5 femtomoles.

2. The method of claim 1, wherein the high fidelity PCR product is a cDNA.

3. The method of claim 1, wherein the high fidelity PCR product is generated by performing three cycles of PCR.

4. The method of claim 1, wherein cloning a high fidelity PCR product into a vector is accomplished by direct cloning into the vector.

5. The method of claim 1, wherein cloning a high fidelity PCR product into a vector is accomplished by indirect cloning into the vector.

6. The method of claim 1, wherein cloning a high fidelity PCR product into a vector comprises purifying the high fidelity PCR product.

7. The method of claim 1, wherein cloning a high fidelity PCR product into a vector comprises digesting the nucleic acid with a restriction enzyme.

8. The method of claim 1, wherein cloning a high fidelity PCR product into a vector is accomplished by directly hybridizing to the vector.

9. The method of claim 1, wherein cloning a high fidelity PCR product into a vector is accomplished by recombination into the vector.

10. The method of claim 1, wherein cloning a high fidelity PCR product into a vector comprises using a reagent selected from the group consisting of:
(a) a ligase;
(b) a recombinase;
(c) a topoisomerase;
(d) an adaptor;
(e) a linker; and
(f) a bridge primer hybridizing to both the high fidelity PCR product and the vector.

11. A method of cloning a high fidelity primer extension product comprising: providing a target nucleic acid as a template for primer extension; generating a high fidelity primer extension product from 1–10 doublings of the target nucleic acid by performing 1–10 cycles of primer extension; and cloning a copy of the target nucleic acid into a vector;
wherein the target nucleic acid is provided in an amount no greater than about 0.5 femtomoles.

12. The method of claim 11, wherein the high fidelity primer extension product is a cDNA.

13. The method of claim 11, wherein cloning a high fidelity primer extension product into a vector is accomplished by direct cloning into the vector.

14. The method of claim 11, wherein cloning a high fidelity primer extension product into a vector is accomplished by indirect cloning into the vector.

15. The method of claim 11, wherein cloning a high fidelity primer extension product into a vector comprises purifying the high fidelity primer extension product.

16. The method of claim 11, wherein cloning a high fidelity primer extension product into a vector comprises digesting the nucleic acid with a restriction enzyme.

17. The method of claim 11, wherein cloning a high fidelity primer extension product into a vector is accomplished by directly hybridizing to the vector.

18. The method of claim 11, wherein cloning a high fidelity primer extension product into a vector is accomplished by recombination into the vector.

19. The method of claim 11, wherein cloning a high fidelity primer extension product into a vector comprises using a reagent selected from the group consisting of:
(a) a ligase;
(b) a recombinase;
(c) a topoisomerase;
(d) an adaptor;
(e) a linker; and
(f) a bridge primer hybridizing to both the copy of the target nucleic acid and the vector.

* * * * *